United States Patent [19]

Yoshigi et al.

[11] Patent Number: 5,688,684
[45] Date of Patent: Nov. 18, 1997

[54] RECOMBINANT β-AMYLASE

[75] Inventors: Naohiro Yoshigi; Hideo Maeba; Yukio Okada, all of Yaizu, Japan

[73] Assignee: Sapporo Breweries Ltd., Tokyo, Japan

[21] Appl. No.: 531,601

[22] Filed: Sep. 21, 1995

[30] Foreign Application Priority Data

Sep. 28, 1994 [JP] Japan .................................. 6-233086

[51] Int. Cl.⁶ ............................ C12N 1/20; C12N 15/00; C07H 21/04
[52] U.S. Cl. ............................. 435/252.33; 435/320.1; 536/23.2
[58] Field of Search .......................... 435/20.1, 320.1, 435/252.33; 536/23.2

[56] References Cited

U.S. PATENT DOCUMENTS 5,273,762  12/1993  Ahvenainen et al. .................. 426/11
5,312,739   5/1994  Shaw ............................... 435/95

OTHER PUBLICATIONS

Oyo Toshitsu Kagaku, vol. 41, No. 2, pp. 261–271, 1994, Naohiro Yoshigi, et al., "Structure of Barley B–Amylase and Expression in *Escherichia coli* of cDNA".

Eur. J. Biochem., vol. 169, pp. 517–525, 1987, Martin Kreis, et al., "Primary Structure and Differential Expression of B-Amylase in Normal and Mutant Barleys".

Biosci. Biotech. Biochem., vol. 58, No. 6, pp. 1080–1086, 1994, Naohiro Yoshigi, et al., "Expression in *Escherichia coli* of cDNA Encoding Barley B–Amylase and Properties of Recombinant B–Amylase".

J. Biochem., vol. 115, pp. 47–51, 1994, Naohiro Yoshigi, et al., "PCR Cloning and Sequencing of the B–Amylase cDNA from Barley".

J. Biochem., vol. 118, pp. 562–567, 1995, Naohiro Yoshigi, et al., "Construction of a Plasmid Used for the Expression of a Sevenfold–Mutant Barley B–Amylase with Increased Thermostability in *Escherichia coli* and Properties of the Sevenfold–Mutant B–Amylase".

*Primary Examiner*—Robert A. Wax
*Assistant Examiner*—Lisa J. Hobbs
*Attorney, Agent, or Firm*—Oblon, Spivak, McClelland, Maier & Neustadt, P.C.

[57] ABSTRACT

A recombinant β-amylase which is superior to the original recombinant β-amylase in thermostability has been obtained by a site-directed mutagenesis with the recombinant β-amylase gene coding 531 amino acid residues. Substitutions were $MET_{181}$ of said enzyme with Leu, $Ser_{291}$ with Ala, $Ile_{293}$ with Val, $Ser_{346}$ with Pro, $Ser_{347}$ with Pro, $Gln_{348}$ with Asp and $Ala_{372}$ with Ser.

6 Claims, 3 Drawing Sheets

RECOMBINANT β-AMYLASE

BACKGROUND OF THE INVENTION

1. Field of the Invention

This invention relates to a β-amylase with an improved thermostability as well as an improved enzyme stability in the alkaline pH region, a gene coding the enzyme and an expression vector containing the gene.

2. Description of the Related Art

Barley β-Amylase

Barley β-amylase is a β-amylase (1,4-α-D-glucan maltohydrolase [EC 3.2.1.2]) obtained from barley seeds and is well known along with soybean β-amylase, as a useful enzyme for the industrial maltose production used for transfusional solutions and foodstuffs.

However, since barley is one of the principal agricultural products for the production of livestock feeds and beverages (such as beer and whisky), from the viewpoint of the global food situation in the future it is not advisable to consume the harvested barley as a source of β-amylase.

Therefore, the method for producing β-amylase in microorganisms using genetic engineering techniques has been given attention as an other source of this enzyme than the barley. If the efficient expression of the barley β-amylase gene in a microorganism is accomplished, the steady supply of inexpensive β-amylase will become possible, obviously contributing a great deal to the maltose production.

Gene of Barley β-Amylase

As to the barley β-amylase gene, the cDNA consisted of 1754 base pairs of cultivar Hiproly has been reported, and also the amino acid sequence consisted of 535 residues has been deduced (Eur. J. Biochem., 169, 517 (1987)). In addition, the cDNA consisted of 1775 base pairs of cultivar Haruna Nijo has been reported, and also the amino acid sequence consisted of 535 residues has been established (J. Biochem., 115, 47 (1994)).

In studies on β-amylase of cultivar Haruna Nijo, the expression vector (pBETA92) was already constructed by inserting a DNA fragment, which was prepared by deleting 55 base pairs of a full-length cDNA from its 5'-terminus and linking a SmaI linker, into the SmaI site of plasmid pKK223-3 (Pharmacia Biotech). Also the production of recombinant β-amylase has been accomplished by transforming *Escherichia coli* JM109 (Toyobo) with said expression vector and expressing the recombinant β-amylase gene therein. Furthermore, it was reported that the recombinant β-amylase comprising 531 amino acids showed almost the same properties as barley β-amylase (JP Hei6-58119; JP Hei6-303988).

However, a production of recombinant β-amylase in microorganisms which shows almost the same properties to those of β-amylase from barley seeds is not sufficient for the purpose. It is because of the fact that, since soybean β-amylase is somewhat superior to barley β-amylase in thermostability, soybean β-amylase is more widely used in practice. Therefore, in order to improve the utility value of the barley β-amylase, it is necessary to provide it at least with the similar function (thermostability) to that of soybean β-amylase.

As to the barley recombinant β-amylases with improved thermostability by protein engineering, it has been proved that a double-mutant β-amylase wherein $Ser_{291}$ of the enzyme is replaced with Ala, and $Ser_{346}$ is replaced with Pro, by site-directed mutagenesis, is superior to the original recombinant β-amylase (JP Hei6-126151).

To further improve the utility value of recombinant β-amylase, it is necessary to construct β-amylase with a further improved thermostability by protein engineering.

SUMMARY OF THE INVENTION

The present invention aims to construct a gene encoding a recombinant β-amylase with a further improved thermostability site-directed mutagenesis, provide a recombinant vector containing the gene, transform microorganisms with the vector and eventually provide recombinant β-amylase with a further improved thermostability.

As a result of studies to further improve the thermostability of β-amylase without changing the enzymatic function thereof, the inventors of the present invention have found that a sevenfold-mutant enzyme comprising the substitutions of $Met_{181}$ by Leu, $Ile_{293}$ by Val, $Ser_{347}$ by Pro, $Gln_{348}$ by Asp and $Ala_{372}$ by Ser in addition to those of $Ser_{291}$ by Ala and $Ser_{346}$ by Pro (JP Hei6-126151) was much superior to the double-mutant enzyme in thermostability accomplishing the present invention.

That is, the recombinant β-amylase according to the present invention is that comprising the amino acid sequence denoted by SEQ ID NO: 1.

β-Amylase according to the present invention is a recombinant β-amylase which acts on polysaccharides having α-1,4-glucoside linkages such as soluble starch, amylose and amylopectin in addition to maltooligosaccharides with a degree of polymerization higher than 3 liberating successively a β-maltose unit from the non-reducing ends thereof, shows more than 80% of the maximum enzymatic activity at pH 3.5–7.0 (37° C.), retains more than 80% remaining activity after the treatment for 1 h at pH 3.5–12.5 (37° C.), shows the maximum activity toward soluble starch at 65° C. and 87% of the maximum activity at 70° C. (pH 7.0), and is stable after treatment for 30 min at up to 62.5° C. in the absence of a substrate at pH 7.0.

Furthermore, the gene of the present invention is the gene encoding recombinant β-amylase comprising the amino acid sequence of SEQ ID NO: 1.

The gene according to the present invention is the gene encoding recombinant β-amylase of Claim 1 having the nucleotide sequence of SEQ ID NO: 2.

The expression vector according to the present invention is the expression vector for β-amylase comprising any one of the genes described above. An Expression vector of this sort is exemplified by that having the nucleotide sequence of SEQ ID NO: 3.

Host cells according to the present invention are those containing the expression vectors.

In the following, there will be described the practical method for preparing recombinant β-amylase according to the present invention, a gene encoding the enzyme and an expression vector containing the gene.

1. Base Substitution of β-Amylase Expression Vector pBETA92 By Site-Directed Mutagenesis The base substitution at the specific site of the gene sequence of β-amylase expression vector pBETA92 can be achieved by site-directed mutagenesis (Anal. Biochem., 200, 81 (1992)).

2. Transformation Host Microorganism With β-Amylase Expression Vector

Any microorganisms can be used as the host cell so far as the expression vector for β-amylase with the improved thermostability can proliferate stably and autonomously therein.

As to the method to transform the host microorganism with the expression vector for recombinant β-amylase, any published method, for example, the competent cell method (J. Mol. Biol., 58, 159 (1970)) may be used in the case where the host microorganism is *Escherichia coli*.

3. Confirmation of DNA Sequence

DNA sequence can be performed by the chemical modification method according to Maxam-Gilbert (Methods in Enzymology, 65, 499 (1980)) or the dideoxynucleotide chain termination method (Gene, 19, 269 (1982)) or the like.

Furthermore, the amino acid sequence of β-amylase according to the present invention can be deduced from the DNA sequence.

4. Production and Purification of Recombinant β-Amylase

After growing the host microorganism harboring the β-amylase expression vector for a certain period, the pure preparation of recombinant β-amylase can be obtained by cell lysis, if necessary, followed by a combination of ammonium sulfate fractionation and various chromatographies such as gel filtration or ion exchange.

β-Amylase activity may be assayed using 2,4-dichlorophenyl β-maltopentaoside (Ono Pharmaceutical) as the substrate. In this case, one unit of enzyme is defined as the amount of enzyme which produces 1 μmol of dichlorophenol per min at 37° C.

5. Estimation of Thermostability

An aliquot of enzyme preparation (30 μl each) in 1.5-ml Eppendorf tubes was incubated at temperatures ranging from 50°–72.5° C. (at 2.5° C.-intervals) in a water bath for 30 min. The remaining activity was assayed using 20 μl aliquot withdrawn from the tube. The remaining activity versus temperature curves were used to determine the temperature curves of enzyme relative at which 50% of the initial activity was lost during 30-min heating period and half-inactivation temperature values provided a parameter for the ranking of thermal stabilities of the enzyme.

Soybean β-amylase used as a control is one purchased from Amano Pharmaceutical (trade name, Biozyme M-5). The enzyme preparation was diluted using a solution of 50 mM Good's buffer (pH 7.0)/1% bovine serum albumin.

Studies of effects of temperature and pH on β-amylase activity were done by reacting the enzyme with soluble starch at pH 7.0. The amount of the reducing sugar produced was measured by the dinitrosalicylic acid method (Denpun Kagaku Handbook, Asakurashoten, p. 188–189 (1977)), and 1 unit of the enzyme was defined as the amount which liberates 1 μmol of maltose per min.

6. Determination of Optimum pH

The reaction mixture, 0.4 ml of 1% soluble starch solution, 0.2 ml of various buffers (described below) and 0.2 ml of enzyme preparation, was incubated at 37° C. The amount of reducing sugars produced was measured by the dinitrosalicylic acid method, and results were expressed as the value relative to the maximum activity (100%). As a result of measuring the optimum pH in this manner, the optimum pH at which the enzyme shows more than 80% of the maximum activity was found to be in the range of 3.5–7.0.

Buffers used were as follows:

| pH 2.5 ≈ 3.0 | Citrate buffer |
|---|---|
| pH 3.5 ≈ 5.5 | Acetate buffer |
| pH 6.0 ≈ 8.0 | Good's buffer |
| pH 8.5 | Tris-maleate buffer |
| pH 9.0 ≈ 11.0 | Glycine buffer |

7. Determination of pH Stability

To the enzyme preparation (50 μl) was added 100 mM various buffers (50 μl) and the mixture was incubated at 37° C. for 1 h. Then 0.9 ml of 500 mM Good's buffer (pH 7.0)/1% bovine serum albumin solution was added. To 0.4 ml aliquot withdrawn was added 0.4 ml of 1% soluble starch solution (pH 7.0), and the mixture was incubated at 37° C. and the remaining enzymatic activity was measured. As a result of measuring pH stability in this manner, the pH range where more than 80% of the original activity was stably retained was found to be 3.5–12.5.

Buffers used were as follows:

| pH 3.0 | Citrate buffer |
|---|---|
| pH 3.5 ≈ 5.5 | Acetate buffer |
| pH 6.0 ≈ 8.0 | Good's buffer |
| pH 8.5 | Tris-maleate buffer |
| pH 9.0 ≈ 11.5 | Glycine buffer |
| pH 12.0 ≈ 13.0 | KCl—NaOH buffer |

DESCRIPTION OF THE PREFERRED EMBODIMENT

Figure 1:
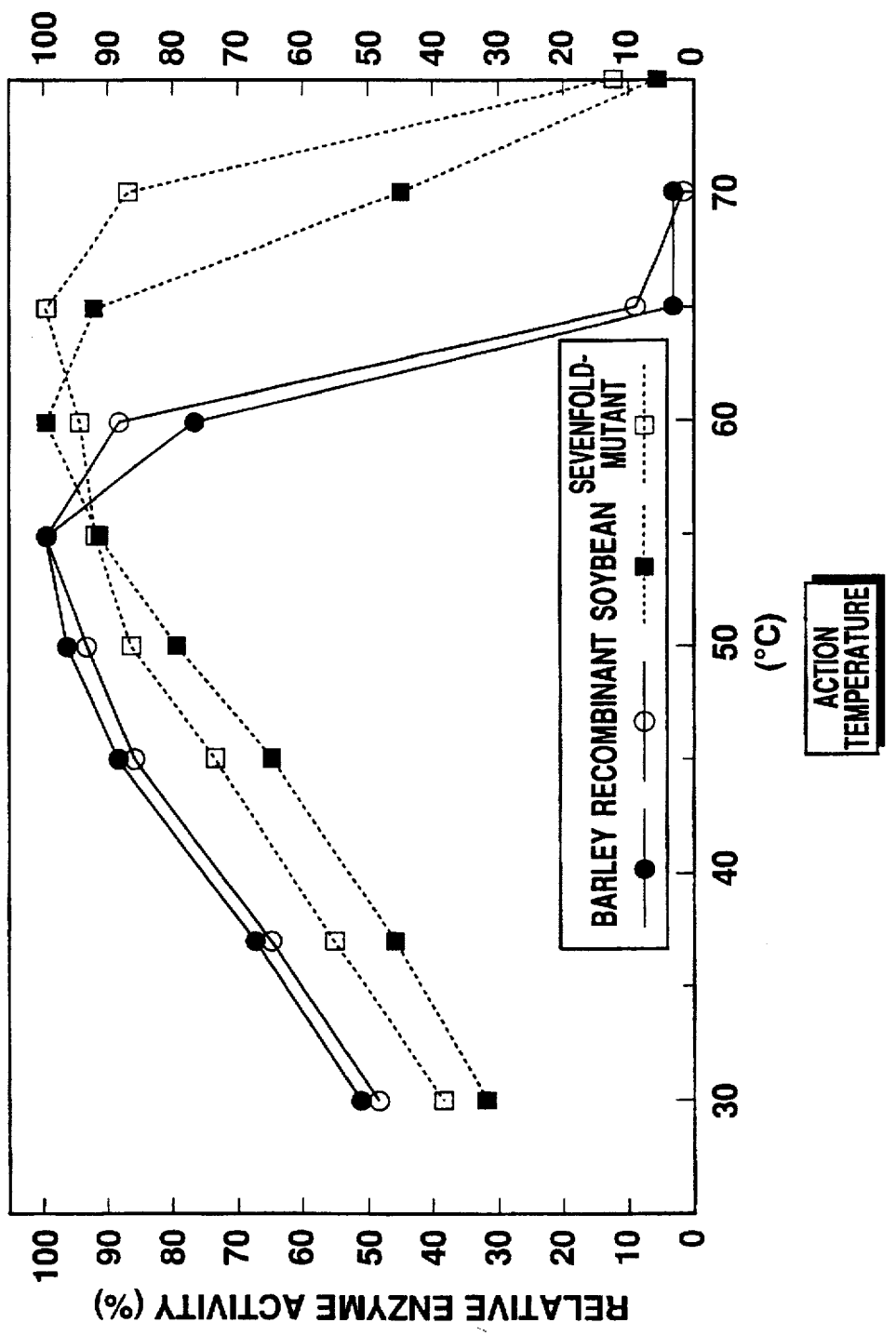
FIG. 1 is a drawing showing the optimum temperature of each preparation. In the figure, (□ . . . □) indicates sevenfold-mutant β-amylase according to the present invention, (●-●) barley β-amylase, (○-○) original recombinant β-amylase and (■ . . . ■) soybean β-amylase.

The invention will now be described in further detail with reference to specific examples, however, it is understood that the scope of the present invention is not to be construed as being limited to them in any way.

EXAMPLE 1

Base Substitution of the Recombinant Wild-Type β-Amylase Expression Vector By Site-Directed Mutagenesis The site-directed mutagenesis was done using a Transfer Site-directed Mutagenesis kit (Clontech Laboratories).

Using the following four mutagenesis primers 5'-AGCTGGAGAGTTGAGGTACCC-3' (for $Met_{181}$ to Leu; SEQ ID NO: 4), 5'-AATCAAGATCGCTGGCGTTCACTGGTG-3' (for $Ser_{291}$ to Ala and $Ile_{293}$ to Val; SEQ ID NO: 5), 5'-TTCGGAGCAACCCCCGGACGCGATGAGCGCA-3' (for $Ser_{346}$ to Pro, $Ser_{347}$ to Pro and $Gln_{348}$ to Asp; SEQ ID NO: 6) and 5'-CCTAAATGTGTCATGCGAAAA-3' (for $Ala_{372}$ to Ser; SEQ ID NO: 7) and the selection primer 5'-GGTTGAGTATTCACCAGTC-3' (SEQ ID NO: 8), the site-directed mutagenesis was done according to the manual provided with the kit to obtain the recombinant β-amylase (sevenfold-mutant β-amylase) expression vector (pBETA92/sevenfold-mutant) as shown in SEQ ID NO: 3.

EXAMPLE 2

Determination of DNA Sequence

DNA sequence confirmed that, as shown in SEQ ID NO: 2 in the sequence list, $A_{541}$ was substituted with T, $T_{871}$ with G. $A_{877}$ with G, $AG_{1036-1037}$ with CC, $T_{1039}$ with C, $C_{1042}$ with G, $G_{1044}$ with C and $G_{1114}$ with T. Consequently, it was confirmed that the expression vector pBETA92/sevenfold-mutant is encoding the recombinant β-amylase as shown in SEQ ID NO: 1 of the sequence list.

EXAMPLE 3

Production and Purification of Recombinant β-Amylase

*Escherichia coli* JM109 harboring the expression vector pBETA92/sevenfold-mutant was grown in a liquid medium (containing 1% Tryptone, 0.5% yeast extract, 1% NaCl, 0.005% Ampicillin Na and 0.1 mM isopropyl β-D-thiogalactopyranoside in 400 ml of water, pH 7.0) at 37° C. for 24 h. After centrifugation to remove the culture medium, packed cells were suspended in a lysozyme solution (0.025% lysozyme, 20 mM Tris-HCl and 30 mM NaCl, pH 7.5) for 30 min on ice, and disrupted by sonication (50 W, 30 sec) followed by centrifugation.

To the above crude extract was added solid ammonium sulfate to 30% saturation. After the precipitate was removed by centrifugation, the supernatant was loaded onto a Butyl Toyopearl 650S (Toso) column (2.5×18.5 cm). The active fractions which were eluted with 50 mM acetate buffer (pH 5.5) were collected and dialyzed against 15 mM Tris-HCl (pH 8.0). The dialyzed solution was centrifuged to remove insoluble materials and then loaded onto a DEAE-Toyopearl 650S (Toso) column (2.5×18.5 cm). The active fractions which were eluted with 15 mM Tris-HCl (pH 8.0)/50 mM NaCl were collected, and added solid ammonium sulfate to 70% saturation. The precipitate formed were collected by centrifugation, dissolved in 50 mM acetate buffer (pH 5.5) and then dialyzed against the same buffer. Then the dialyzed solution was loaded onto a Toyopearl HW-50S (Toso) column (1.5×48.5 cm). The active fractions which were eluted with 50 mM acetate buffer (pH 5.5) were combined as the purified preparation of the recombinant β-amylase. On SDS-polyacrylamide gel electrophoresis the purified preparation showed a single protein band at an apparent molecular weight of 56,000 which migrated to almost the same position as the original recombinant β-amylase.

EXAMPLE 4

Enzymatic Properties of Sevenfold-Mutant β-Amylase

Comparison of the enzymatic properties of the sevenfold-mutant β-amylase with those of the original recombinant β-amylase revealed that both enzymes were similar except for the optimum temperature, thermostability and pH stability.

Results of studies on the optimum temperature are shown in FIG. 1. In contrast to the barley β-amylase and the original recombinant β-amylase which showed the maximum activity at 55° C. and almost no activity at 65°–70° C. the sevenfold-mutant β-amylase was found to show the maximum activity at 65° C. and a significant activity even at 70° C. It was also confirmed that the sevenfold-mutant β-amylase was significantly improved in thermostability as compared with the soybean β-amylase which showed the maximum activity at 60° C.

Figure 2:
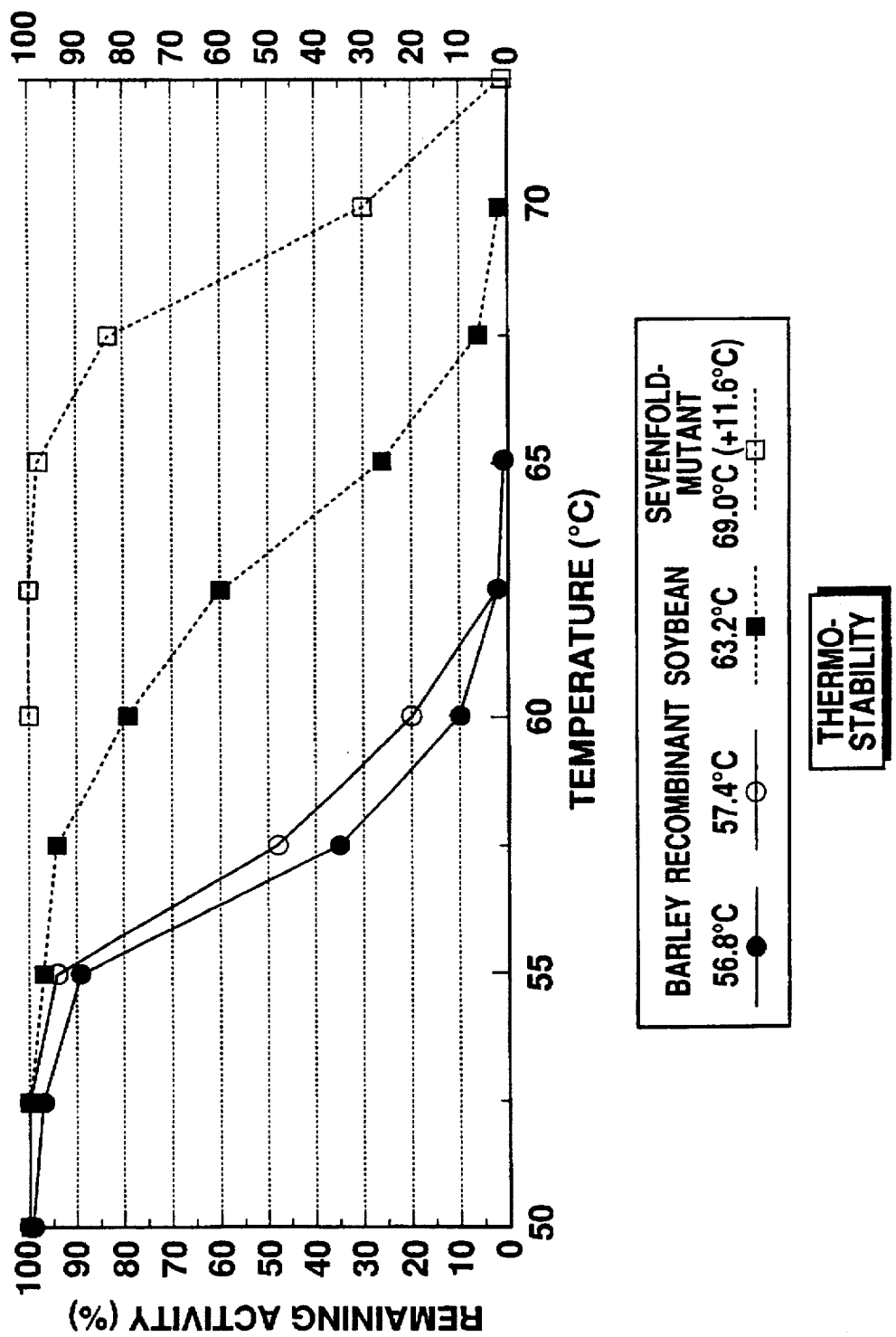
FIG. 2 is a drawing showing the thermostability of each preparation. In the figure, (□ . . . □) indicates sevenfold-mutant β-amylase according to the present invention, (●-●) barley β-amylase, (○-○) original recombinant β-amylase and (■ . . . ■) soybean β-amylase.

From heat-inactivation curves shown in FIG. 2, temperatures at which 50% of the initial activity was lost during a 30 min heating time were found as follows:

| | |
|---|---|
| barley β-amylase | → 56.8° C. |
| original recombinant β-amylase | → 57.4° C. |
| sevenfold-mutant β-amylase | → 69.0° C. |
| soybean β-amylase | → 63.2° C. |

The results indicate that the thermostability of the sevenfold-β-amylase was improved by 11.6° C. than that of the original recombinant β-amylase, and furthermore by 5.8° C. than that of the soybean β-amylase.

A great deal improvement of the sevenfold-mutant β-amylase in the thermostability was confirmed by the fact that, while the original recombinant β-amylase was almost completely inactivated by treatment at 62.5° C. for 30 min, the sevenfold-mutant β-amylase was not inactivated at all by the same treatment.

Figure 3:
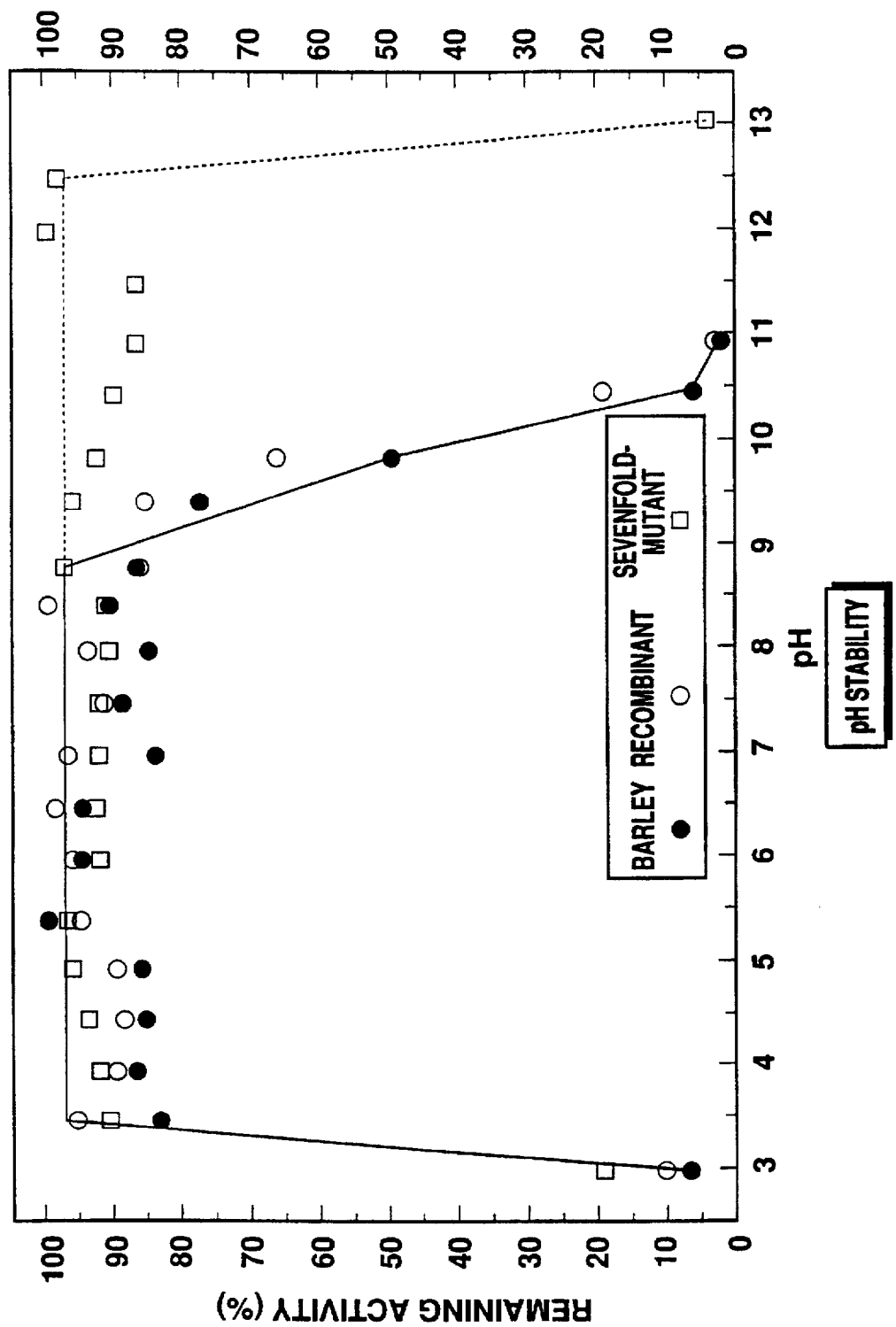
FIG. 3 is a drawing showing the pH stability of each preparation. In the figure, (□ . . . □) indicates sevenfold-mutant β-amylase according to the present invention, (●-●) barley β-amylase and (○-○) original recombinant β-amylase.

As to the pH stability, as shown in FIG. 3, while the barley B-amylase and the original recombinant B-amylase were stable in the pH range of 3.5–9.5, the sevenfold-mutant β-amylase was stable in the pH range of 3.5–12.5, indicating a significant improvement in the stability of the latter β-amylase in the alkaline pH range.

The present invention has made it possible to produce a recombinant β-amylase with improved thermostability as well as improved enzyme stability in the alkaline pH range.

---

What is claimed is:

1. An isolated gene coding for a recombinant β-amylase having an amino acid sequence denoted by SEQ ID NO: 1.

2. An isolated gene coding for a recombinant β-amylase according to claim 1 and having a nucleic acid sequence denoted by SEQ ID NO: 2.

3. A β-amylase expression vector comprising the gene according to claim 1.

4. A host cell harboring the expression vector according to claim 3.

5. A recombinant β-amylase expression vector comprising the gene according to claim 2.

6. A host cell harboring the expression vector according to claim 5.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
　　　　( A ) LENGTH: 531 amino acids
　　　　( B ) TYPE: amino acid
　　　　( C ) STRANDEDNESS: single
　　　　( D ) TOPOLOGY: linear ( i i ) MOLECULE TYPE: protein ( x i ) SEQUENCE DESCRIPTION: SEQ ID NO:1:

Met　Lys　Gly　Asn　Tyr　Val　Gln　Val　Tyr　Val　Met　Leu　Pro　Leu　Asp　Ala

-continued

|  | 1 |  |  |  | 5 |  |  |  | 10 |  |  |  | 15 |  |
|---|---|---|---|---|---|---|---|---|---|---|---|---|---|---|
| Val | Ser | Val | Asn | Asn | Arg | Phe | Glu | Lys | Gly | Asp | Glu | Leu | Arg | Ala | Gln |
|  |  |  | 20 |  |  |  |  | 25 |  |  |  | 30 |  |  |
| Leu | Arg | Lys | Leu | Val | Glu | Ala | Gly | Val | Asp | Gly | Val | Met | Val | Asp | Val |
|  |  | 35 |  |  |  | 40 |  |  |  |  | 45 |  |  |  |
| Trp | Trp | Gly | Leu | Val | Glu | Gly | Lys | Gly | Pro | Lys | Ala | Tyr | Asp | Trp | Ser |
|  | 50 |  |  |  | 55 |  |  |  |  | 60 |  |  |  |  |
| Ala | Tyr | Lys | Gln | Leu | Phe | Glu | Leu | Val | Gln | Lys | Ala | Gly | Leu | Lys | Leu |
| 65 |  |  |  | 70 |  |  |  | 75 |  |  |  |  |  | 80 |
| Gln | Ala | Ile | Met | Ser | Phe | His | Gln | Cys | Gly | Gly | Asn | Val | Gly | Asp | Ala |
|  |  |  | 85 |  |  |  | 90 |  |  |  |  |  | 95 |  |
| Val | Asn | Ile | Pro | Ile | Pro | Gln | Trp | Val | Arg | Asp | Val | Gly | Thr | Arg | Asp |
|  |  | 100 |  |  |  | 105 |  |  |  |  | 110 |  |  |  |
| Pro | Asp | Ile | Phe | Tyr | Thr | Asp | Gly | His | Gly | Thr | Arg | Asn | Ile | Glu | Tyr |
|  | 115 |  |  |  | 120 |  |  |  |  | 125 |  |  |  |  |
| Leu | Thr | Leu | Gly | Val | Asp | Asn | Gln | Pro | Leu | Phe | His | Gly | Arg | Ser | Ala |
|  | 130 |  |  |  | 135 |  |  |  |  | 140 |  |  |  |  |
| Val | Gln | Met | Tyr | Ala | Asp | Tyr | Met | Thr | Ser | Phe | Arg | Glu | Asn | Met | Lys |
| 145 |  |  |  | 150 |  |  |  | 155 |  |  |  |  |  | 160 |
| Asp | Phe | Leu | Asp | Ala | Gly | Val | Ile | Val | Asp | Ile | Glu | Val | Gly | Leu | Gly |
|  |  |  | 165 |  |  |  | 170 |  |  |  |  |  | 175 |  |
| Pro | Ala | Gly | Glu | Leu | Arg | Tyr | Pro | Ser | Tyr | Pro | Gln | Ser | His | Gly | Trp |
|  |  | 180 |  |  |  | 185 |  |  |  |  | 190 |  |  |  |
| Ser | Phe | Pro | Gly | Ile | Gly | Glu | Phe | Ile | Cys | Tyr | Asp | Lys | Tyr | Leu | Gln |
|  | 195 |  |  |  | 200 |  |  |  |  | 205 |  |  |  |  |
| Ala | Asp | Phe | Lys | Ala | Ala | Ala | Ala | Val | Gly | His | Pro | Glu | Trp | Glu |
| 210 |  |  |  | 215 |  |  |  |  | 220 |  |  |  |  |  |
| Phe | Pro | Asn | Asp | Ala | Gly | Gln | Tyr | Asn | Asp | Thr | Pro | Glu | Arg | Thr | Gln |
| 225 |  |  |  | 230 |  |  |  | 235 |  |  |  |  |  | 240 |
| Phe | Phe | Arg | Asp | Asn | Gly | Thr | Tyr | Leu | Ser | Glu | Lys | Gly | Arg | Phe | Phe |
|  |  |  | 245 |  |  |  | 250 |  |  |  |  |  | 255 |  |
| Leu | Ala | Trp | Tyr | Ser | Asn | Asn | Leu | Ile | Lys | His | Gly | Asp | Arg | Ile | Leu |
|  |  | 260 |  |  |  | 265 |  |  |  |  | 270 |  |  |  |
| Asp | Glu | Ala | Asn | Lys | Val | Phe | Leu | Gly | Tyr | Lys | Val | Gln | Leu | Ala | Ile |
|  | 275 |  |  |  | 280 |  |  |  |  | 285 |  |  |  |  |
| Lys | Ile | Ala | Gly | Val | His | Trp | Trp | Tyr | Lys | Val | Pro | Ser | His | Ala | Ala |
| 290 |  |  |  | 295 |  |  |  |  | 300 |  |  |  |  |  |
| Glu | Leu | Thr | Ala | Gly | Tyr | Tyr | Asn | Leu | His | Asp | Arg | Asp | Gly | Tyr | Arg |
| 305 |  |  |  | 310 |  |  |  | 315 |  |  |  |  |  | 320 |
| Thr | Ile | Ala | Arg | Met | Leu | Lys | Arg | His | Arg | Ala | Ser | Ile | Asn | Phe | Thr |
|  |  |  | 325 |  |  |  | 330 |  |  |  |  |  | 335 |  |
| Cys | Ala | Glu | Met | Arg | Asp | Ser | Glu | Gln | Pro | Pro | Asp | Ala | Met | Ser | Ala |
|  |  | 340 |  |  |  | 345 |  |  |  |  | 350 |  |  |  |
| Pro | Glu | Glu | Leu | Val | Gln | Gln | Val | Leu | Ser | Ala | Gly | Trp | Arg | Glu | Gly |
|  | 355 |  |  |  | 360 |  |  |  |  | 365 |  |  |  |  |
| Leu | Asn | Val | Ser | Cys | Glu | Asn | Ala | Leu | Pro | Arg | Tyr | Asp | Pro | Thr | Ala |
|  | 370 |  |  |  | 375 |  |  |  |  | 380 |  |  |  |  |
| Tyr | Asn | Thr | Ile | Leu | Arg | Asn | Ala | Arg | Pro | His | Gly | Ile | Asn | Gln | Ser |
| 385 |  |  |  | 390 |  |  |  | 395 |  |  |  |  |  | 400 |
| Gly | Pro | Pro | Glu | His | Lys | Leu | Phe | Gly | Phe | Thr | Tyr | Leu | Arg | Leu | Ser |
|  |  |  | 405 |  |  |  | 410 |  |  |  |  |  | 415 |  |
| Asn | Gln | Leu | Val | Glu | Gly | Gln | Asn | Tyr | Val | Asn | Phe | Lys | Thr | Phe | Val |
|  |  |  | 420 |  |  |  | 425 |  |  |  |  |  | 430 |  |

|  |  | Asp | Arg | Met<br>435 | His | Ala | Asn | Leu | Pro<br>440 | Arg | Asp | Pro | Tyr | Val<br>445 | Asp | Pro | Met |
|---|---|---|---|---|---|---|---|---|---|---|---|---|---|---|---|---|---|
|  |  | Ala | Pro<br>450 | Leu | Pro | Arg | Ser | Gly<br>455 | Pro | Glu | Ile | Ser | Ile<br>460 | Glu | Met | Ile | Leu |
|  |  | Gln<br>465 | Ala | Ala | Gln | Pro | Lys<br>470 | Leu | Gln | Pro | Phe | Pro<br>475 | Phe | Gln | Glu | His | Thr<br>480 |
|  |  | Asp | Leu | Pro | Val | Gly<br>485 | Pro | Thr | Gly | Gly | Met<br>490 | Gly | Gly | Gln | Ala | Glu<br>495 | Gly |
|  |  | Pro | Thr | Cys | Gly<br>500 | Met | Gly | Gly | Gln | Val<br>505 | Lys | Gly | Pro | Thr | Gly<br>510 | Gly | Met |
|  |  | Gly | Gly | Gln<br>515 | Ala | Glu | Asp | Pro | Thr<br>520 | Ser | Gly | Met | Gly | Gly<br>525 | Glu | Leu | Pro |
|  |  | Ala | Thr | Met<br>530 |  |  |  |  |  |  |  |  |  |  |  |  |  |

( 2 ) INFORMATION FOR SEQ ID NO:2:

( i ) SEQUENCE CHARACTERISTICS:
        ( A ) LENGTH: 1596 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:2:

| GTGAAAGGCA | ACTATGTCCA | AGTCTACGTC | ATGCTCCCTC | TGGACGCCGT | GAGCGTGAAC | 60 |
|---|---|---|---|---|---|---|
| AACAGGTTCG | AGAAGGGCGA | CGAGCTGAGG | GCGCAATTGA | GGAAGCTGGT | AGAGGCCGGT | 120 |
| GTGGATGGTG | TCATGGTAGA | CGTCTGGTGG | GGCTTGGTGG | AGGGCAAGGG | CCCCAAGGCG | 180 |
| TATGACTGGT | CCGCCTACAA | GCAGTTGTTT | GAGCTGGTGC | AGAAGGCTGG | GCTGAAGCTA | 240 |
| CAGGCCATCA | TGTCGTTCCA | CCAGTGTGGT | GGCAACGTCG | GCGACGCCGT | CAACATCCCA | 300 |
| ATCCCACAGT | GGGTGCGGGA | CGTCGGCACG | CGTGATCCCG | ACATTTTCTA | CACCGACGGT | 360 |
| CACGGGACTA | GGAACATTGA | GTACCTCACT | CTTGGAGTTG | ATAACCAGCC | TCTCTTCCAT | 420 |
| GGAAGATCTG | CCGTCCAGAT | GTATGCCGAT | TACATGACAA | GCTTCAGGGA | GAACATGAAA | 480 |
| GACTTCTTGG | ATGCTGGTGT | TATCGTCGAC | ATTGAAGTGG | GACTTGGCCC | AGCTGGAGAG | 540 |
| TTGAGGTACC | CATCATATCC | TCAGAGCCAC | GGATGGTCGT | TCCCAGGCAT | CGGAGAATTC | 600 |
| ATCTGCTATG | ATAAATACCT | ACAAGCAGAC | TTCAAAGCAG | CAGCAGCGGC | GGTCGGCCAT | 660 |
| CCTGAGTGGG | AATTTCCTAA | CGATGCCGGA | CAGTACAATG | ACACTCCCGA | GAGAACTCAA | 720 |
| TTCTTCAGGG | ACAACGGGAC | ATACCTAAGT | GAGAAGGGGA | GGTTTTTCCT | TGCATGGTAC | 780 |
| TCCAACAATC | TGATCAAGCA | CGGTGACAGG | ATCTTGGATG | AAGCAAACAA | GGTCTTCTTG | 840 |
| GGATACAAGG | TGCAATTGGC | AATCAAGATC | GCTGGCGTTC | ACTGGTGGTA | CAAGGTTCCA | 900 |
| AGCCATGCAG | CCGAGCTCAC | AGCTGGGTAC | TATAACTTAC | ATGATAGAGA | CGGCTACAGA | 960 |
| ACCATAGCAC | GCATGCTCAA | AAGGCACCGT | GCTAGCATTA | ACTTCACTTG | CGCGGAGATG | 1020 |
| AGGGATTCGG | AGCAACCCCC | GGACGCGATG | AGCGCACCAG | AAGAACTAGT | CCAACAGGTG | 1080 |
| TTGAGTGCTG | GATGGAGAGA | GGGCCTAAAT | GTGTCATGCG | AAAACGCGCT | TCCACGATAT | 1140 |
| GATCCAACTG | CTTACAACAC | CATACTCAGG | AATGCGAGGC | CTCATGGAAT | CAACCAGAGC | 1200 |
| GGCCCTCCTG | AGCACAAGCT | GTTTGGATTC | ACCTACCTTC | GGCTGTCGAA | TCAGCTGGTG | 1260 |
| GAGGGACAAA | ACTATGTCAA | CTTCAAGACC | TTTGTCGACA | GAATGCATGC | CAACCTGCCT | 1320 |
| CGTGACCCAT | ATGTTGATCC | AATGGCGCCC | TTGCCAAGAT | CAGGGCCAGA | AATATCGATT | 1380 |

-continued

| | | | | | |
|---|---|---|---|---|---|
| GAGATGATCC | TACAAGCAGC | ACAGCCAAAA | CTGCAGCCAT | TCCCCTTCCA | GGAGCACACC | 1440
| GACCTGCCAG | TAGGCCCTAC | TGGTGGCATG | GGTGGGCAGG | CTGAAGGCCC | CACCTGTGGC | 1500
| ATGGGTGGGC | AAGTTAAAGG | CCCTACTGGT | GGCATGGGTG | GGCAGGCTGA | AGACCCTACT | 1560
| AGTGGCATGG | GTGGGAGCT | CCCTGCCACC | ATGTAA | | | 1596

(2) INFORMATION FOR SEQ ID NO:3:

(i) SEQUENCE CHARACTERISTICS:
        (A) LENGTH: 6312 base pairs
        (B) TYPE: nucleic acid
        (C) STRANDEDNESS: double
        (D) TOPOLOGY: circular (ii) MOLECULE TYPE: DNA (genomic)

(xi) SEQUENCE DESCRIPTION: SEQ ID NO:3:

| | | | | | |
|---|---|---|---|---|---|
| TTCCGGGATG | GAGGTGAACG | TGAAAGGCAA | CTATGTCCAA | GTCTACGTCA | TGCTCCCTCT | 60
| GGACGCCGTG | AGCGTGAACA | ACAGGTTCGA | GAAGGGCGAC | GAGCTGAGGG | CGCAATTGAG | 120
| GAAGCTGGTA | GAGGCCGGTG | TGGATGGTGT | CATGGTAGAC | GTCTGGTGGG | GCTTGGTGGA | 180
| GGGCAAGGGC | CCCAAGGCGT | ATGACTGGTC | CGCCTACAAG | CAGTTGTTTG | AGCTGGTGCA | 240
| GAAGGCTGGG | CTGAAGCTAC | AGGCCATCAT | GTCGTTCCAC | CAGTGTGGTG | GCAACGTCGG | 300
| CGACGCCGTC | AACATCCCAA | TCCCACAGTG | GGTGCGGGAC | GTCGGCACGC | GTGATCCCGA | 360
| CATTTTCTAC | ACCGACGGTC | ACGGGACTAG | GAACATTGAG | TACCTCACTC | TTGGAGTTGA | 420
| TAACCAGCCT | CTCTTCCATG | GAAGATCTGC | CGTCCAGATG | TATGCCGATT | ACATGACAAG | 480
| CTTCAGGGAG | AACATGAAAG | ACTTCTTGGA | TGCTGGTGTT | ATCGTCGACA | TTGAAGTGGG | 540
| ACTTGGCCCA | GCTGGAGAGT | TGAGGTACCC | ATCATATCCT | CAGAGCCACG | GATGGTCGTT | 600
| CCCAGGCATC | GGAGAATTCA | TCTGCTATGA | TAAATACCTA | CAAGCAGACT | TCAAAGCAGC | 660
| AGCAGCGGCG | GTCGGCCATC | CTGAGTGGGA | ATTTCCTAAC | GATGCCGGAC | AGTACAATGA | 720
| CACTCCCGAG | AGAACTCAAT | TCTTCAGGGA | CAACGGGACA | TACCTAAGTG | AGAAGGGGAG | 780
| GTTTTTCCTT | GCATGGTACT | CCAACAATCT | GATCAAGCAC | GGTGACAGGA | TCTTGGATGA | 840
| AGCAAACAAG | GTCTTCTTGG | GATACAAGGT | GCAATTGGCA | ATCAAGATCG | CTGGCGTTCA | 900
| CTGGTGGTAC | AAGGTTCCAA | GCCATGCAGC | CGAGCTCACA | GCTGGGTACT | ATAACTTACA | 960
| TGATAGAGAC | GGCTACAGAA | CCATAGCACG | CATGCTCAAA | AGGCACCGTG | CTAGCATTAA | 1020
| CTTCACTTGC | GCGGAGATGA | GGGATTCGGA | GCAACCCCCG | GACGCGATGA | GCGCACCAGA | 1080
| AGAACTAGTC | CAACAGGTGT | TGAGTGCTGG | ATGGAGAGAG | GGCCTAAATG | TGTCATGCGA | 1140
| AAACGCGCTT | CCACGATATG | ATCCAACTGC | TTACAACACC | ATACTCAGGA | ATGCGAGGCC | 1200
| TCATGGAATC | AACCAGAGCG | GCCCTCCTGA | GCACAAGCTG | TTTGGATTCA | CCTACCTTCG | 1260
| GCTGTCGAAT | CAGCTGGTGG | AGGGACAAAA | CTATGTCAAC | TTCAAGACCT | TTGTCGACAG | 1320
| AATGCATGCC | AACCTGCCTC | GTGACCCATA | TGTTGATCCA | ATGGCGCCCT | TGCCAAGATC | 1380
| AGGGCCAGAA | ATATCGATTG | AGATGATCCT | ACAAGCAGCA | CAGCCAAAAC | TGCAGCCATT | 1440
| CCCCTTCCAG | GAGCACACCG | ACCTGCCAGT | AGGCCCTACT | GGTGGCATGG | GTGGGCAGGC | 1500
| TGAAGGCCCC | ACCTGTGGCA | TGGGTGGGCA | AGTTAAAGGC | CCTACTGGTG | GCATGGGTGG | 1560
| GCAGGCTGAA | GACCCTACTA | GTGGCATGGG | TGGGAGCTC | CCTGCCACCA | TGTAATGGAA | 1620
| CCTTTATGAT | TTACTACCCT | TTATGTTGTG | TGTGAGTGTG | ACAGAGAAAC | CTTTCTCTGC | 1680
| CTTATTAATA | ATAAATAAAG | CACATCACTT | GTGTGTGTTC | TGAAAAGCCC | GGGGATCCGT | 1740
| CGACCTGCAG | CCAAGCTTGG | CTGTTTTGGC | GGATGAGAGA | AGATTTTCAG | CCTGATACAG | 1800

```
ATTAAATCAG AACGCAGAAG CGGTCTGATA AAACAGAATT TGCCTGGCGG CAGTAGCGCG   1860
GTGGTCCCAC CTGACCCCAT GCCGAACTCA GAAGTGAAAC GCCGTAGCGC CGATGGTAGT   1920
GTGGGGTCTC CCCATGCGAG AGTAGGGAAC TGCCAGGCAT CAAATAAAAC GAAAGGCTCA   1980
GTCGAAAGAC TGGGCCTTTC GTTTTATCTG TTGTTTGTCG GTGAACGCTC TCCTGAGTAG   2040
GACAAATCCG CCGGGAGCGG ATTTGAACGT TGCGAAGCAA CGGCCCGGAG GGTGGCGGGC   2100
AGGACGCCCG CCATAAACTG CCAGGCATCA AATTAAGCAG AAGGCCATCC TGACGGATGG   2160
CCTTTTTGCG TTTCTACAAA CTCTTTTGTT TATTTTTCTA AATACATTCA AATATGTATC   2220
CGCTCATGAG ACAATAACCC TGATAAATGC TTCAATAATA TTGAAAAAGG AAGAGTATGA   2280
GTATTCAACA TTTCCGTGTC GCCCTTATTC CCTTTTTTGC GGCATTTTGC CTTCCTGTTT   2340
TTGCTCACCC AGAAACGCTG GTGAAAGTAA AAGATGCTGA AGATCAGTTG GGTGCACGAG   2400
TGGGTTACAT CGAACTGGAT CTCAACAGCG GTAAGATCCT TGAGAGTTTT CGCCCCGAAG   2460
AACGTTTTCC AATGATGAGC ACTTTTAAAG TTCTGCTATG TGGCGCGGTA TATCCCGTG    2520
TTGACGCCGG GCAAGAGCAA CTCGGTCGCC GCATACACTA TTCTCAGAAT GACTTGGTTG   2580
AGTATTCACC AGTCACAGAA AAGCATCTTA CGGATGGCAT GACAGTAAGA GAATTATGCA   2640
GTGCTGCCAT AACCATGAGT GATAACACTG CGGCCAACTT ACTTCTGACA ACGATCGGAG   2700
GACCGAAGGA GCTAACCGCT TTTTGCACA ACATGGGGGA TCATGTAACT CGCCTTGATC    2760
GTTGGGAACC GGAGCTGAAT GAAGCCATAC CAAACGACGA GCGTGACACC ACGATGCCTG   2820
TAGCAATGGC AACAACGTTG CGCAAACTAT TAACTGGCGA ACTACTTACT CTAGCTTCCC   2880
GGCAACAATT AATAGACTGG ATGGAGGCGG ATAAAGTTGC AGGACCACTT CTGCGCTCGG   2940
CCCTTCCGGC TGGCTGGTTT ATTGCTGATA AATCTGGAGC CGGTGAGCGT GGGTCTCGCG   3000
GTATCATTGC AGCACTGGGG CCAGATGGTA AGCCCTCCCG TATCGTAGTT ATCTACACGA   3060
CGGGGAGTCA GGCAACTATG GATGAACGAA ATAGACAGAT CGCTGAGATA GGTGCCTCAC   3120
TGATTAAGCA TTGGTAACTG TCAGACCAAG TTTACTCATA TATACTTTAG ATTGATTTAA   3180
AACTTCATTT TTAATTTAAA AGGATCTAGG TGAAGATCCT TTTTGATAAT CTCATGACCA   3240
AAATCCCTTA ACGTGAGTTT TCGTTCCACT GAGCGTCAGA CCCCGTAGAA AAGATCAAAG   3300
GATCTTCTTG AGATCCTTTT TTTCTGCGCG TAATCTGCTG CTTGCAAACA AAAAAACCAC   3360
CGCTACCAGC GGTGGTTTGT TTGCCGGATC AAGAGCTACC AACTCTTTTT CCGAAGGTAA   3420
CTGGCTTCAG CAGAGCGCAG ATACCAAATA CTGTCCTTCT AGTGTAGCCG TAGTTAGGCC   3480
ACCACTTCAA GAACTCTGTA GCACCGCCTA CATACCTCGC TCTGCTAATC CTGTTACCAG   3540
TGGCTGCTGC CAGTGGCGAT AAGTCGTGTC TTACCGGGTT GGACTCAAGA CGATAGTTAC   3600
CGGATAAGGC GCAGCGGTCG GGCTGAACGG GGGGTTCGTG CACACAGCCC AGCTTGGAGC   3660
GAACGACCTA CACCGAACTG AGATACCTAC AGCGTGAGCA TTGAGAAAGC GCCACGCTTC   3720
CCGAAGGGAG AAAGGCGGAC AGGTATCCGG TAAGCGGCAG GGTCGGAACA GGAGAGCGCA   3780
CGAGGGAGCT TCCAGGGGGA AACGCCTGGT ATCTTTATAG TCCTGTCGGG TTTCGCCACC   3840
TCTGACTTGA GCGTCGATTT TTGTGATGCT CGTCAGGGGG GCGGAGCCTA TGGAAAAACG   3900
CCAGCAACGC GGCCTTTTTA CGGTTCCTGG CCTTTTGCTG GCCTTTTGCT CACATGTTCT   3960
TTCCTGCGTT ATCCCCTGAT TCTGTGGATA ACCGTATTAC CGCCTTTGAG TGAGCTGATA   4020
CCGCTCGCCG CAGCCGAACG ACCGAGCGCA GCGAGTCAGT GAGCGAGGAA GCGGAAGAGC   4080
GCCTGATGCG GTATTTTCTC CTTACGCATC TGTGCGGTAT TCACACCGC ATATGGTGCA    4140
CTCTCAGTAC AATCTGCTCT GATGCCGCAT AGTTAAGCCA GTATACACTC CGCTATCGCT   4200
```

-continued

```
ACGTGACTGG GTCATGGCTG CGCCCCGACA CCCGCCAACA CCCGCTGACG CGCCCTGACG      4260
GGCTTGTCTG CTCCCGGCAT CCGCTTACAG ACAAGCTGTG ACCGTCTCCG GGAGCTGCAT      4320
GTGTCAGAGG TTTTCACCGT CATCACCGAA ACGCGCGAGG CAGCTGCGGT AAAGCTCATC      4380
AGCGTGGTCG TGAAGCGATT CACAGATGTC TGCCTGTTCA TCCGCGTCCA GCTCGTTGAG      4440
TTTCTCCAGA AGCGTTAATG TCTGGCTTCT GATAAAGCGG GCCATGTTAA GGGCGGTTTT      4500
TTCCTGTTTG GTCACTTGAT GCCTCCGTGT AAGGGGGAAT TTCTGTTCAT GGGGGTAATG      4560
ATACCGATGA AACGAGAGAG GATGCTCACG ATACGGGTTA CTGATGATGA ACATGCCCGG      4620
TTACTGGAAC GTTGTGAGGG TAAACAACTG GCGGTATGGA TGCGGCGGGA CCAGAGAAAA      4680
ATCACTCAGG GTCAATGCCA GCGCTTCGTT AATACAGATG TAGGTGTTCC ACAGGGTAGC      4740
CAGCAGCATC CTGCGATGCA GATCCGGAAC ATAATGGTGC AGGGCGCTGA CTTCCGCGTT      4800
TCCAGACTTT ACGAAACACG GAAACCGAAG ACCATTCATG TTGTTGCTCA GGTCGCAGAC      4860
GTTTTGCAGC AGCAGTCGCT TCACGTTCGC TCGCGTATCG GTGATTCATT CTGCTAACCA      4920
GTAAGGCAAC CCCGCCAGCC TAGCCGGGTC CTCAACGACA GGAGCACGAT CATGCGCACC      4980
CGTGGCCAGG ACCCAACGCT GCCCGAGATG CGCCGCGTGC GGCTGCTGGA GATGGCGGAC      5040
GCGATGGATA TGTTCTGCCA AGGGTTGGTT TGCGCATTCA CAGTTCTCCG CAAGAATTGA      5100
TTGGCTCCAA TTCTTGGAGT GGTGAATCCG TTAGCGAGGT GCCGCCGGCT TCCATTCAGG      5160
TCGAGGTGGC CCGGCTCCAT GCACCGCGAC GCAACGCGGG GAGGCAGACA AGGTATAGGG      5220
CGGCGCCTAC AATCCATGCC AACCCGTTCC ATGTGCTCGC CGAGGCGGCA TAAATCGCCG      5280
TGACGATCAG CGGTCCAGTG ATCGAAGTTA GGCTGGTAAG AGCCGCGAGC GATCCTTGAA      5340
GCTGTCCCTG ATGGTCGTCA TCTACCTGCC TGGACAGCAT GGCCTGCAAC GCGGGCATCC      5400
CGATGCCGCC GGAAGCGAGA AGAATCATAA TGGGGAAGGC CATCCAGCCT CGCGTCGCGA      5460
ACGCCAGCAA GACGTAGCCC AGCGCGTCGG CCGCCATGCC GGCGATAATG GCCTGCTTCT      5520
CGCCGAAACG TTTGGTGGCG GGACCAGTGA CGAAGGCTTG AGCGAGGGCG TGCAAGATTC      5580
CGAATACCGC AAGCGACAGG CCGATCATCG TCGCGCTCCA GCGAAAGCGG TCCTCGCCGA      5640
AAATGACCCA GAGCGCTGCC GGCACCTGTC CTACGAGTTG CATGATAAAG AAGACAGTCA      5700
TAAGTGCGGC GACGATAGTC ATGCCCGCG  CCCACCGGAA GGAGCTGACT GGGTTGAAGG      5760
CTCTCAAGGG CATCGGTCGA CGCTCTCCCT TATGCGACTC CTGCATTAGG AAGCAGCCCA      5820
GTAGTAGGTT GAGGCCGTTG AGCACCGCCG CCGCAAGGAA TGGTGCATGC AAGGAGATGG      5880
CGCCCAACAG TCCCCCGGCC ACGGGGCCTG CCACCATACC CACGCCGAAA CAAGCGCTCA      5940
TGAGCCCGAA GTGGCGAGCC CGATCTTCCC CATCGGTGAT GTCGGCGATA TAGGCGCCAG      6000
CAACCGCACC TGTGGCGCCG GTGATGCCGG CCACGATGCG TCCGGCGTAG AGGATCCGGG      6060
CTTATCGACT GCACGGTGCA CCAATGCTTC TGGCGTCAGG CAGCCATCGG AAGCTGTGGT      6120
ATGGCTGTGC AGGTCGTAAA TCACTGCATA ATTCGTGTCG CTCAAGGCGC ACTCCCGTTC      6180
TGGATAATGT TTTTGCGCC  GACATCATAA CGGTTCTGGC AAATATTCTG AAATGAGCTG      6240
TTGACAATTA ATCATCGGCT CGTATAATGT GTGGAATTGT GAGCGGATAA CAATTTCACA      6300
CAGGAAACAG AA                                                          6312
```

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single ( D ) TOPOLOGY: linear ( i i ) MOLECULE TYPE: other nucleic acid
            ( A ) DESCRIPTION: /desc ="SYNTHETIC DNA"

( x i ) SEQUENCE DESCRIPTION: SEQ ID NO:4:

AGCTGGAGAG TTGAGGTACC C          21

( 2 ) INFORMATION FOR SEQ ID NO:5:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc ="SYNTHETIC DNA"

( x i ) SEQUENCE DESCRIPTION: SEQ ID NO:5:

AATCAAGATC GCTGGCGTTC ACTGGTG          27

( 2 ) INFORMATION FOR SEQ ID NO:6:

( i ) SEQUENCE CHARACTERISTICS:
            ( A ) LENGTH: 31 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc ="SYNTHETIC DNA"

( x i ) SEQUENCE DESCRIPTION: SEQ ID NO:6:

TTCGGAGCAA CCCCCGGACG CGATGAGCGC A          31

( 2 ) INFORMATION FOR SEQ ID NO:7:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc ="SYNTHETIC DNA"

( x i ) SEQUENCE DESCRIPTION: SEQ ID NO:7:

CCTAAATGTG TCATGCGAAA A          21

( 2 ) INFORMATION FOR SEQ ID NO:8:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc ="SYNTHETIC DNA"

( x i ) SEQUENCE DESCRIPTION: SEQ ID NO:8:

GGTTGAGTAT TCACCAGTC          19